(12) United States Patent
Argentieri

(10) Patent No.: US 7,015,242 B2
(45) Date of Patent: Mar. 21, 2006

(54) METHODS FOR TREATING HYPERACTIVE GASTROINTESTINAL MOTILITY

(75) Inventor: Thomas M. Argentieri, Yardley, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/635,081

(22) Filed: Aug. 6, 2003

(65) Prior Publication Data

US 2004/0029949 A1 Feb. 12, 2004

Related U.S. Application Data

(62) Division of application No. 10/114,148, filed on Apr. 2, 2002, now abandoned
(60) Provisional application No. 60/281,471, filed on Apr. 4, 2001.

(51) Int. Cl.
*A61K 31/404* (2006.01)

(52) U.S. Cl. ........................................ 514/418; 514/411
(58) Field of Classification Search ................ 514/418, 514/411
See application file for complete search history.

(56) References Cited

U.S. PATENT DOCUMENTS

| | | | |
|---|---|---|---|
| 5,384,330 A | 1/1995 | Dieter et al. | |
| 5,565,483 A | 10/1996 | Hewawasam et al. | |
| 5,602,169 A | 2/1997 | Hewawasam et al. | |
| 5,849,789 A | 12/1998 | Rostock et al. | |
| 5,852,053 A | 12/1998 | Rostock et al. | |
| 5,914,425 A | 6/1999 | Meisel et al. | |
| 6,117,900 A | 9/2000 | Rundfeldt et al. | |
| 6,348,486 B1 | 2/2002 | Argentieri et al. | |
| 6,596,759 B1 | 7/2003 | Abe et al. | |
| 2002/0111379 A1 | 8/2002 | Wyeth | |

FOREIGN PATENT DOCUMENTS

| | | |
|---|---|---|
| EP | 0 539 153 A1 | 4/1993 |
| EP | 0 747 354 A1 | 12/1996 |
| WO | WO 00/33834 A1 | 6/2000 |
| WO | WO 01/01970 A2 | 1/2001 |
| WO | WO 02/00217 A1 | 1/2002 |
| WO | WO 02/49628 A2 | 6/2002 |

OTHER PUBLICATIONS

Toja et al., Arzneimittelforschung, Apr., 1994, 44(4), 501–9.*
Hennig et al., Journal of Physiology, (1999), 517/2, pp. 575–590.*
Schroder, Rikke et al., Neuropharmacology, 40, 888–898 (2001).
Sims, Stephen et al., J. Physiol., 367, 503–529 (1985).
A. Wei et al., Neuropharmacology, 35(7), 805–829 (1996).
C. Rundfeldt, Neuroscience Letters, 282, 73–76 (2000).
C. Rundfeldt, Epilepsy Research, 35, 99–107 (1999).
Martin J. Main et al., Molecular Pharmacology, 58, 253–262 (2000).

* cited by examiner

*Primary Examiner*—Phyllis G. Spivack
(74) *Attorney, Agent, or Firm*—Kimberly R. Hild

(57) ABSTRACT

This invention provides methods for the treatment or inhibition of hyperactive gastrointestinal motility in a mammal utilizing compounds having the formula:

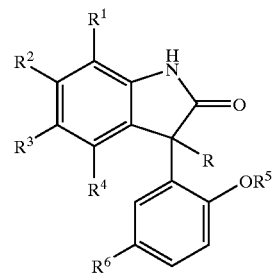

where R, and $R^1$ to $R^6$ are described herein.

9 Claims, No Drawings

METHODS FOR TREATING HYPERACTIVE GASTROINTESTINAL MOTILITY

This application is a divisional of U.S. application Ser. No. 10/114,148 filed on Apr. 2, 2002, now abandoned, which in turn claims the benefit of U.S. Provisional application Ser. No. 60/281,471, filed Apr. 4, 2001. The entire disclosures of the No. 60/281,471 and Ser. No. 10/114,148 applications are hereby incorporated by reference.

This invention relates to novel methods for modulating gastrointestinal tissues utilizing compounds which modulate the KCNQ family of potassium channels, particularly compounds which open or agonize the channels. The methods of this invention include the treatment, prevention, inhibition and amelioration of hyperactive gastrointestinal motility, including that associated with colitis, Irritable Bowel Syndrome and Crohn's Disease.

BACKGROUND OF THE INVENTION

U.S. Pat. No. 5,384,330 (Dieter et al.) teaches pharmacologically active 1,2,4-triaminobenzene derivatives of the General Formula:

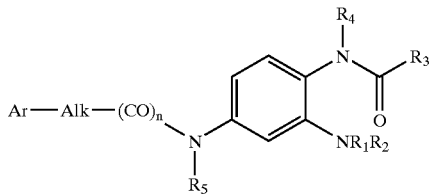

and their properties as anti-epileptic, muscle relaxing, fever-reducing and peripheral analgesic agents.

U.S. Pat. No. 5,565,483 (Hewawasam et al.) teaches compounds of the formulae:

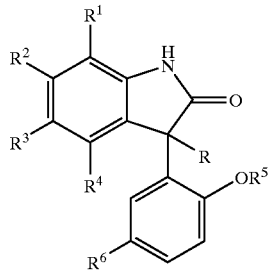

wherein: R is hydrogen, hydroxy or fluoro; $R^1$, $R^2$, $R^3$ and $R^4$ each are independently hydrogen, $C_{1-4}$ alkyl, halogen, trifluoromethyl, phenyl, p-methylphenyl or p-trifluoromethylphenyl; or $R^1$ and $R^2$, $R^2$ and $R^3$ or $R^3$ and $R^4$ are joined together to form a benzo fused ring; $R^5$ is hydrogen or $C_{1-4}$ alkyl; and $R^6$ is chlorine or trifluoromethyl; or a nontoxic pharmaceutically acceptable salt, solvate or hydrate thereof, which are potassium channel openers useful for treating ischemia, convulsions and asthma.

The article *Modulation of KCNQ2/3 Potassium Channels by the Novel Anticonvulsant Retigabine*, Main et al., Molecular Pharmacology, 58: pp. 253–262, 2000, describes the actions of retigabine (D23129; N-[2-amino-4-(4-fluorobenzylamino)-phenyl]carbamic acid ethyl ester) in modulating the KCNQ2/3 potassium channels in oocytes in a 3-fold manner, i.e. retigabine shifts the voltage dependence of channel activation to more hyperpolarized membrane potentials, increases the rate of channel activation and slows channel deactivation.

U.S. Pat. Nos. 5,849,789 and 5,852,053 (both to Rostock et al.) teaches the use of retigabine for the treatment of neurodegenerative disorders, including those associated with stroke.

U.S. Pat. No. 5,914,425 (Meisel et al.) teaches novel crystalline forms of retigabine.

U.S. Pat. No. 6,117,900 teaches the use of retigabine, also known as N-[2-amino-4-(4-fluorobenzylamino)-phenyl] carbamic acid ethyl ester, for the treatment of neuropathic pain.

DESCRIPTION OF THE INVENTION

This invention comprises methods for treating, preventing, inhibiting, alleviating or controlling hyperactive gastrointestinal motility in a mammal, the methods comprising administering to a mammal in need thereof a pharmaceutically effective amount of a compound which acts as an agonist or opener of the KCNQ family of potassium channels, including the KCNQ2, KCNQ3, KCNQ4, and KCNQ5 potassium channels, alone or in combination. A particular embodiment of this invention includes use in the methods described herein of one or more agonists or openers of KCNQ2/3 potassium channels. Another series of methods of this invention comprises use of one or more agonists or openers of KCNQ3/5 potassium channels. Further methods of this invention comprise treatment of the bladder instability conditions described herein by pharmaceutical administration of one or more agonists or openers of KCNQ4 potassium channels.

Specific methods of this invention include the treatment, prevention, inhibition, alleviation or control of hyperactive gastrointestinal motility associated with colitis, irritable bowel syndrome (IBS) or Crohn's Disease.

Among the compounds useful in the methods of this invention are those disclosed in U.S. Pat. No. 5,384,330 (Dieter et al.), the contents of which are incorporated herein by reference. The compounds include those of the formula:

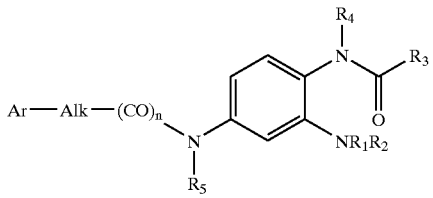

wherein:
$R_1$ is selected from hydrogen, $C_1$–$C_6$-alkyl, $C_2$–$C_6$-alkanoyl or the radical Ar;

$R_2$ is selected from hydrogen or $C_1$–$C_6$-alkyl;

$R_3$ is selected from $C_1$–$C_6$-alkoxy, $NH_2$, $C_1$–$C_6$-alkylamino, $C_1$–$C_6$-dialkylamino, amino substituted by the radical Ar, $C_1$–$C_6$-alkyl, $C_{2-6}$-alkenyl, $C_2$–$C_6$-alkynyl, the radical Ar or the radical ArO—;

$R_4$ is selected from hydrogen, $C_1$–$C_6$-alkyl or the radical Ar;

$R_5$ is selected from hydrogen or $C_1$–$C_6$-alkyl or the radical Ar;

Alk indicates a straight or branched alkylene group with 1–9 carbon atoms, which can also be substituted by the radical Ar;

Ar is a phenyl radical substituted by the radicals $R_6$, $R_7$ and/or $R_8$ where these radicals $R_6$, $R_7$ and $R_8$ are the same or different and represent H, $C_1$–$C_6$-alkyl, $C_3$–$C_7$-cycloalkyl, hydroxy, $C_1$–$C_6$-alkoxy, $C_2$–$C_6$-alkanoyloxy, halogen, hydroxy, $C_1$–$C_6$-halogenoalkyl, —CN, —$NH_2$, —NH—$C_1$–$C_6$-alkyl, —N($C_1$–$C_6$-alkyl)$_2$, —$CO_2$H, —CO—$C_1$–$C_6$-alkyl, —CO—O—$C_1$–$C_6$-alkyl, —COAr, —CO—OAr, —$CONH_2$, —CONH—$C_1$–$C_6$-alkyl, —CON($C_1$–$C_6$-alkyl)$_2$, —CONHAr, —NH—CO—$C_1$–$C_6$-alkyl, —NHCO—

Ar, —NHCO—$C_1$-$C_6$-alkoxy, —N—H—CO—Ar, —NHCO—$NH_2$, —NHCO—N(—$C_1$-$C_6$-alkyl)$_2$, —NHCO—NHAr, —NH—$SO_2$—C-1-$C_6$-alkyl, —NH—$SO_2$Ar, —NH—$SO_2$-nitrophenyl, —$SO_2$—OH, —$SO_2$—$C_1$-$C_6$-alkyl, —$SO_2$—Ar, —$SO_2$—$C_1$-$C_6$-alkoxy, —$SO_2$—OAr, —$SO_2$—$NH_2$, —$SO_2$—NH—$C_1$-$C_6$-alkyl, —$SO_2$—N($C_1$-$C_6$-alkyl)$_2$, —$SO_2$—NHAr, —$SO_2$—$C_1$-$C_6$-alkoxy;

n is 0 or 1;

or a pharmaceutically acceptable salt thereof.

The alkyl groups, halogenalkyl groups, alkenyl groups, alkynyl groups, alkoxy groups, alkylamino groups, alkanoyl amino groups, alkanoyloxy groups and alkanoyl groups in general can be straight or branched. The same also applies to alkyl and alkyloxy groups (=alkoxy groups) if these are components of more complicated radicals for example in the form of a monoalkyl-or dialkylamino group, alkanoylamino group, carbalkoxy group, alkylcarbonyl group and analogous groups. The $C_3$-$C_7$-cycloalkyl group is preferably cyclopentyl or cyclohexyl. $C_2$-$C_6$-alkenyl preferably represents allyl. $C_2$-$C_6$-alkynyl preferably represents propargyl.

The halogen atoms are chlorine, bromine or fluorine, in particular chlorine of fluorine. The alkyl and alkoxy groups as such or as components of groups of more complicated radicals consist in particular of 1–4 carbon atoms, preferably 1 or 2 carbon atoms. Alkanoyl groups, such as alkanoylamino groups or alkanoyloxy groups consist in particular of 2–4, preferably 2–3 carbon atoms. Alk consists in particular of 1–3, preferably 1 or 2 carbon atoms.

Among the more preferred compounds of this group are:
2-Amino-4-(4-fluorobenzylamino)-1-ethoxycarbonylaminobenzene;
2-Amino-4-(4-trifluoromethylbenzylamino)-1-ethoxycarbonylamino-benzene;
2-Amino-4-benzylamino-1-ethoxycarbonylamino-benzene;
2-Amino-4-(3,5-dichlorobenzylamino)-1-ethoxycarbonylamino benzene;
2-Amino-4-(3,5-dichlorobenzylamino)-1-propyloxycarbonylamino benzene;
2-Amino-(2-chlorobenzylamino)-1-(diethylcarbamoylamino) benzene;
2-Amino-4-(2,4-dichlorobenzylamino)-1-(dimethylcarbamoylamino) benzene; and
1,2-Diacetylamino-4-(4-fluorobenzylamino) benzene;

Among the most preferred compounds for use in the methods of this invention are N-[2-amino-4-(4-fluorobenzylamino)-phenyl]carbamic acid and its pharmaceutically acceptable salts and ester forms. Of particular preference is retigabine, also known as N-[2-amino-4-(4-fluorobenzylamino)-phenyl]carbamic acid ethyl ester (CAS Registry No. 150812-12-7), having the formula:

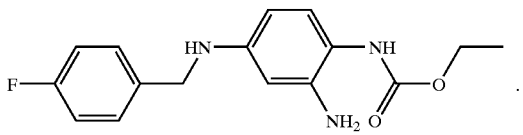

Also useful in the methods of this invention are the metabolite forms of retigabine which may be isolated from blood, urine or feces of recipients of N-[2-amino-4-(4-fluorobenzylamino)-phenyl]carbamic acid ethyl ester. The metabolites include the glucoside of retigabine, [4-(4-Fluoro-benzylamino)-2-(3,4,5-trihydroxy-6-hydroxymethyl-tetrahydropyran-2-ylamino)-phenyl]-carbamic acid ethyl ester, as well as its two glucoronide analogs, 6-[2-Ethoxycarbonylamino-5-(4-fluoro-benzylamino)-phenylamino]-3,4,5-trihydroxy-tetrahydro-pyran-2-carboxylic acid and 6-[(3-Amino-4-ethoxycarbonylamino-phenyl)-(4-fluoro-benzyl)-amino]-3,4,5-trihydroxy-tetrahydro-pyran-2-carboxylic acid. Further metabolites include N-[2-Amino-4-(4-fluoro-benzylamino)-phenyl]acetamide, its cyclized analog (4-Fluoro-benzyl)-2-methyl-1H-benzoimidazol-5-yl)amine and the glucoronide analogs of N-[2-Amino-4-(4-fluoro-benzylamino)-phenyl] acetamide, 6-[(4-Acetylamino-3-amino-phenyl)-(4-fluoro-benzyl)-amino]-3,4,5-trihydroxy-tetrahydro-pyran-2-carboxylic acid and 6-[2-Acetylamino-5-(4-fluoro-benzylamino)-phenylamino]-3,4,5-trihydroxy-tetrahydro-pyran-2-carboxylic acid.

Also useful in the methods of this invention are the substituted 3-phenyl oxindole compounds disclosed in U.S. Pat. No. 5,565,483 (Hewawasam et al.), which issued on Oct. 15, 1996, the contents of which are incorporated herein by reference. These compounds include the substituted 3-phenyl oxindole compounds having the formulae:

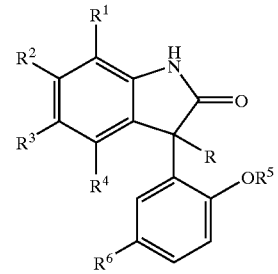

wherein:

R is hydrogen, hydroxy or fluoro;

$R^1$, $R^2$, $R^3$ and $R^4$ each are independently hydrogen, $C_{1-4}$ alkyl, halogen, trifluoromethyl, phenyl, p-methylphenyl or p-trifluoromethylphenyl; or $R^1$ and $R^2$, $R^2$ and $R^3$ or $R^3$ and $R^4$ are joined together to form a benzo fused ring;

$R^5$ is hydrogen or $C_{1-4}$ alkyl; and $R^6$ is chlorine or trifluoromethyl;

or a nontoxic pharmaceutically acceptable salt, solvate or hydrate thereof.

One group of the substituted 3-phenyl oxindole compounds useful with this invention includes those described above wherein R is hydrogen. Another subgroup of these compounds include those in which $R^1$, $R^2$, $R^3$ and $R^4$ are each independently selected from H, $C_1$ to $C_4$ alkyl, halogen or trifluoromethyl, and when $R^1$ and $R^4$ are H; $R^2$ or $R^3$ is phenyl, p-methoxyphenyl or trifluormethylphenyl; or $R^1$ and $R^2$, $R^2$ and $R^3$, or $R^3$ and $R^4$ are joined together to form a benzo fused ring; R5 is H or $C_1$ to $C_4$ alkyl; and $R^6$ is chlorine or trifluoromethyl, or a pharmaceutically acceptable salt form thereof.

Non-limiting examples of these substituted 3-phenyl oxindole compounds are:

(±)-3-(5-Chloro-2-methoxyphenyl)-1,3-dihydro-3-hydroxy-6-(trifluoromethyl)-2H-indol-2-one;

(±)-3-(5-Chloro-2-methoxyphenyl)-1,3-dihydro-6-(trifluoromethyl)-2H-indol-2-one;

(±)-3-(5-Chloro-2-hydroxyphenyl)-1,3-dihydro-3-hydroxy-6-(trifluoromethyl)-2H-indol-2-one;

(±)-3-(5-Chloro-2-hydroxyphenyl)-1,3-dihydro-6-(trifluoromethyl)-2H-indol-2-one;

(±)-3-(5-Chloro-2-hydroxyphenyl)-4,6-dichloro-1,3-dihydro-3-hydroxy-2-H-indol-2-one;

(±)-3-(5-Chloro-2-hydroxyphenyl)-1,3-dihydro-3-hydroxy-7-(trifluoromethyl)-2H-indol-2-one;

(±)-3-(5-Chloro-2-hydroxyphenyl)-1,3-dihydro-3-hydroxy-4-trifluoromethyl)2H-indol-2-one;

(±)-1,3-Dihydro-3-hydroxy-3-[2-hydroxy-5-(trifluoromethyl)phenyl]-6-(trifluoromethyl)-2H-indol-2-one;
(±)-3-(5-Chloro-2-hydroxyphenyl)-1,3-dihydro-3-hydroxy-4,6-bis(trifluoromethyl)-2H-indol-2-one;
(−)-3-(5-Chloro-2-methoxyphenyl)-1,3-dihydro-3-hydroxy-6-(trifluoromethyl)-2H-indol-2-one;
(±)-3-(5-Chloro-2-hydroxyphenyl)-1,3-dihydro-3-hydroxy-6-(trifluoromethyl)2H-indol-2-one;
(−)-3-(5-Chloro-2-hydroxyphenyl)-1,3-dihydro-3-hydroxy-6-(trifluoromethyl)2H-indol-2-one;
(±)-3-(5-Chloro-2-methoxyphenyl)-1,3-dihydro-3-fluoro-6-(trifluoromethyl)2H-indol-2-one;
(±)-3-(5-Chloro-2-hydroxyphenyl)-1,3-dihydro-3-hydroxy-2H-benz[g]indol-2one;
(±)-3-(5-Chloro-2-hydroxyphenyl)-1,3-dihydro-6-phenyl-2H-indol-2-one;
(±)-3-(5-Chloro-2-hydroxyphenyl)-1,3-dihydro-2H-benz[g]indol-2-one;
(±)-3-(5-Chloro-2-methoxyphenyl)-1,3-dihydro-3-fluoro-6-phenyl-2H-indol-2-one;
(±)-3-(5-Chloro-2-methoxyphenyl)-1,3-dihydro-3-fluoro-6-iodo-2H-indol-2one;
(±)-3-(5-Chloro-2-hydroxyphenyl)-1,3-dihydro-6-(4-methylphenyl)-2H-indol-2-one;
(±)-3-(5-Chloro-2-methoxyphenyl)-1,3-dihydro-3-fluoro-7-(trifluoromethyl)-2H-indol-2-one;
(±)-3-(5-Chloro-2-hydroxyphenyl)-1,3-dihydro-2H-benz[e]indol-2-one;
(±)-3-(5-Chloro-2-methoxyphenyl)-1,3-dihydro-3-fluoro-5-methyl-2H-indol-2-one;
(±)-3-(5-Chloro-2-methoxyphenyl)-1,3-dihydro-3-fluoro-4,6-bis(trifluoromethyl)-2H-indol-2-one;
(±)-5-Bromo-3-(5-chloro-2-methoxyphenyl)-1,3-dihydro-3-fluoro-2H-indol-2one;
(±)-3-(5-Chloro-2-hydroxyphenyl)-1,3-dihydro-6-[4-(trifluoromethyl)phenyl]-2H-indol-2-one;
(±)-3-(5-Chloro-2-hydroxyphenyl)-1,3-dihydro-2H-indol-2-one;
(±)-5-Bromo-3-(5-chloro-2-methoxyphenyl)-1,3-dihydro-3-hydroxy-2H-indol-2-one;
(±)-3-(5-Chloro-2-hydroxyphenyl)-4,6-dichloro-1,3-dihydro-2H-indol-2-one;
(±)-3-(5-Chloro-2-methoxyphenyl)-1,3-dihydro-3-hydroxy-6-iodo-2H-indol-2-one;
(±)-3-(5-Chloro-hydroxyphenyl)-1,3-dihydro-6-iodo-2H-indol-2-one;
(±)-3-(5-Chloro-2-methoxyphenyl)-1,3-dihydro-3-hydroxy-2H-benz[f]indol-2one;
(±)-3-(5-Chloro-2-hydroxyphenyl)-1,3-dihydro-3-hydroxy-2H-benz[f]indol-2one; and
(±)-3-(5-Chloro-2-hydroxyphenyl)-1,3-dihydro-2H-benz[f]indol-2-one;
and the pharmaceutically acceptable salt forms thereof.

Among the more preferred compounds of this group are:

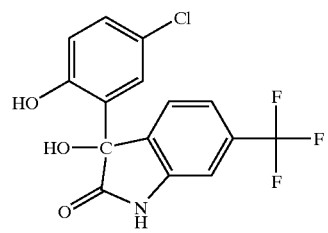

(±)-3-(5-Chloro-2-hydroxyphenyl)-1,3-dihydro-6-(trifluoromethyl)-2H-indol-2-one;

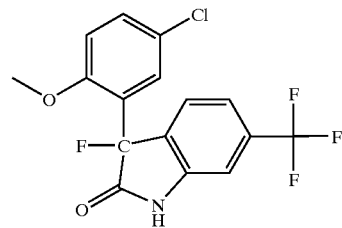

(±)-3-(5-Chloro-2-hydroxyphenyl)-1,3-dihydro-3-hydroxy-6-(trifluoromethyl)-2H-indol-2-one;

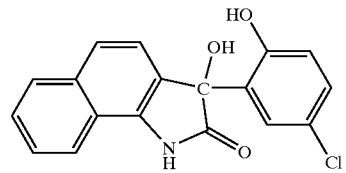

(±)-3-(5-Chloro-2-methoxyphenyl)-1,3-dihydro-3-fluoro-6-(trifluoromethyl)-2H-indol-2-one;

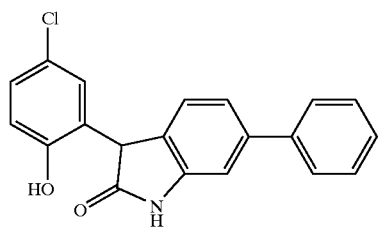

(±)-3-(5-Chloro-2-hydroxyphenyl)-1,3-dihydro-3-hydroxy-2H-benz[g]indol-2-one;

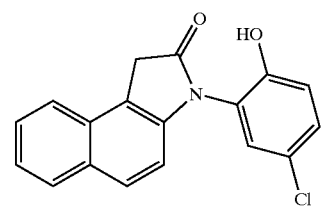

(±)-3-(5-Chloro-2-hydroxyphenyl)-1,3-dihydro-6-phenyl-2H-indol-2-one; and (±)-3-(5-Chloro-2-hydroxyphenyl)-1,3-dihydro-2H-benz[e]indol-2-one.

Pharmaceutically acceptable salt forms of these substituted 3-phenyl oxindole compounds include those formed as base addition, including those formed using suitable inorganic bases, such as alkali and alkaline earth metal bases, such as sodium, potassium, magnesium and calcium metallic cations. The compounds may be administered as described in U.S. Pat. No. 5,565,483. A pharmaceutically effective amount in mammals, including man, may be from about 0.1 pg/kg to about 100 mg/kg of body weight. Parenteral administration may be completed at an effective dose of from about 1 pg/kg to about 10 mg/kg of body weight.

The methods of this invention are useful for treating, preventing, inhibiting or ameliorating hyperactive gastrointestinal motility in a mammal, the methods each comprising administering to a mammal in need of such treatment a pharmaceutically effective amount of a KCNQ potassium channel opener, as described above. The conditions which may be treated with the methods of this invention include irritable bowel syndrome, also known as spastic colon, Crohn's Disease and mucous colitis. The methods of this invention may also be used for mammalian gastrointestinal (GI) conditions including diarrhea, chronic diarrhea, acute diarrhea, abdominal pain associated with diarrhea, postprandial urgency, postprandial accentuation of diarrhea or abdominal pain, or a combination of two or more of these symptoms.

Irritable Bowel Syndrome (IBS) is part of a spectrum of diseases known as Functional Gastrointestinal Disorders, which include diseases such as noncardiac chest pain, non-ulcer dyspepsia, and chronic constipation or diarrhea. It has also been referred to as spastic colon, nervous colitis, mucous colitis, functional colitis or colonic neurosis. As no diagnostic marker is currently associated with IBS, the diagnosis is one of exclusion based on symptoms. Manning et al. first reported six symptoms which differentiated IBS from other gastrointestinal diseases. These criteria have become art recognized in the diagnosis of IBS, see *Gut* 1990; 31: 77–81; Olibuyide et al., *Dig Dis Sci* 1995; 40:983–5; Rao et al., *J Assoc Physician India* 1993;41:357–8; and Jeong et al. *Korean J. Intern. Med.* 1993;8:34–9. The six 'Manning Criteria' are: a) relief of abdominal pain with defecation, b) looser stools with the onset of pain, c) more frequent bowel movements at onset of pain, d) abdominal bloating or distention, e) feelings of incomplete evacuation, and f) passage of mucus per rectum. Generally speaking, the more 'Manning Criteria' present the more likely an indication of IBS.

The compounds and methods of this invention may be used in conjunction with laxatives and anti-diarrheal medications frequently used for the treatment or amelioration of symptoms of IBS. In patients with abdominal cramps, antispasmodic drugs, such as dicyclomine, may be used with the methods herein. It will also be understood that the KCNQ channel opening compounds of this invention may be administered in conjunction with conventional drug therapies for IBS, including opioid agonists such as loperamide or anticholinergic agents, such as pepenzolate bromide or timepidium bromide to control gastrointestinal hypermotility. In cases where anxiety or related conditions increase the likelihood or severity of symptoms, anti-anxiety agents may be co-employed. These include those known in the art, but not limited to venlafaxine HCl, diazepam, fluoxetine HCl, hydroxyzine HCl, hydroxyzine pamoate, mephobarbital, meprobamate, paroxetine HCl, doxepin HCl, lorazepam, chlordiazepoxide HCl, alone or in combination with amitryptyline HCl, clorazepate dipotassium, or alprazolam. Each of these medicaments may be administered in the conventional methods and administrations known in the art, including those described in the Physicians' Desk Reference 2001, 55 Edition, published by Medical Economics Company, Inc. at Montvale, N.J. 07645-1742.

At the recommendation of a medical professional, non-medication and lifestyle changes may also be recommended for IBS sufferers, including an increase in fiber intake (dietary or fiber supplements) to help relieve constipation and cramps.

Crohn's disease involves chronic inflammation of the intestines with symptoms including abdominal pain, diarrhea, and weight loss. Less common symptoms include poor appetite, fever, night sweats, rectal pain, and rectal bleeding. Crohn's disease may affect the colon, the rectum, and the small intestine and, in rare instances, also the stomach, mouth, and esophagus. Crohn's colitis is inflammation that appears only in the colon, often involving abdominal pain and bloody diarrhea. Anal fistulae and perirectal abscesses can also occur. Crohn's enteritis is inflammation confined to the small intestine. Crohn's terminal ileitis is inflammation that affects the end of the small intestine (terminal ileum). Crohn's enterocolitis and ileocolitis involves inflammation of both the small intestine and the colon. Crohn's terminal ileitis and ileocolitis are the most common types of Crohn's disease. Abdominal pain and diarrhea often result in each type of Crohn's disease. The compounds and methods of this invention may be used to treat, inhibit, prevent or ameliorate each of these Crohn's conditions.

The compounds of this invention may also be used in combination therapies or regimens with medications conventionally used to treat Crohn's disease and its symptoms including anti-inflammatory agents, such as 5-ASA compounds, systemic corticosteorids, topical corticosteroids, and antibiotics, as well as immunomodulators. Anti-inflammatory agents which are effective in treating Crohn's disease include corticosteroids and the 5-aminosalycylates (5-ASA) compounds. Examples of corticosteroids include Prednisone, Prednisolone, and Budesonide. Examples of 5-ASA compounds include ASACOL® brand mesalamine, PENTASA® brand mesalamine controlled release capsules, and ROWASA® brand mesalamine rectal suspensions enema. Antibiotics may be used in conjunction to the potassium channel openers of this invention for treating Crohn's colitis, such as metronidazole (available as FLAGLYL® brand metronidazole tablets or FLAGLYL® ER brand extended release metronidazole tablets) and ciprofloxacin. Examples of useful immunomodulators include 6-mercaptopurine (6-MP), azathioprine, methotrexate, and anti-TNF-alpha (REMICADE® infliximab recombinant for IV injection).

In cases where diseased portions of the intestines are surgically removed Crohn's disease may eventually return to previously healthy tissue. The KCNQ potassium channel openers of this invention may be used in conjunction with medications such as mesalamine or 6-mercaptopurine (6-MP) to reduce the chances of Crohn's disease relapse after surgery or limit the severity of such relapses.

In relevant diarrhea-related conditions, a medical professional may also use the KCNQ channel openers of this invention in combination with an inhibitor of gastrointestinal secretion, such as a proton pump inhibitor, a histamin $H_2$-receptor blocker, omeprazole, lansoprazole, cimetidine, ranitidine, nizatidine, or famotidine.

Pharmaceutically effective amounts of the KCNQ channel opening compounds described herein may also be used to inhibit, limit or delay defecation in a mammal in need of such treatment. This may be used to inhibit or control anal incontinence in a mammal, including humans, who experience a lessened ability to control bowel movements or experience or are susceptible to anal incontinence. These methods include effecting a desirable delay or inhibition of postprandial urgency or postprandial intestinal cramping or related pain.

The methods of this invention are useful for inducing or assisting in control or prevention or treatment of the maladies described herein in humans in need of such relief, including adult and pediatric uses. However, they may also be utilized for veterinary applications, particularly including canine and feline fecal control methods. If desired, the methods herein may also be used with farm animals, such as ovine, bovine, porcine and equine breeds.

The applications may utilize conventional oral, rectal, parenteral or intravenous delivery methods as conventionally utilized in veterinary practice. Most preferable in most instance for home use with companion animals are oral tablets or capsules or neat compound or powdered or granular pharmaceutical formulations which may be mixed with chewable or liquid veterinary formulations or food materials or liquids acceptable to the animal in question.

As used herein, the terms "pharmaceutically effective amount" or "therapeutically effective amount" mean the total amount of each active component of the pharmaceutical composition or method that is sufficient to show a meaningful patient benefit, i.e., treatment, prevention or amelioration of hyperactive gastrointestinal motility or the excessive or undesirable urge to defecate, or a decrease in the frequency of incidence of fecal incontinence. When the malady in question warrants, a pharmaceutically or therapeutically effective dose may be considered the minimal amount of the compound in question which will alleviate, inhibit or remove the cramping, pressure, pain or feeling of fecal urgency associated with hyperactive gastrointestinal motility. When applied to an individual active ingredient, administered alone, the term refers to that ingredient alone. When applied to a combination, the term refers to combined amounts of the active ingredients that result in the therapeutic effect, whether administered in combination, serially or simultaneously.

The methods of this invention may be accomplished with a daily dose of the active compounds described above from U.S. Pat. No. 5,384,330 of from about 0.1 mg/kg to about 10 mg/kg. Doses may be administered as a single regimen, such as only prior to bedtime or before travel, or as a continuous regimen divided by two or more doses over the course of a day. Human administration may be at dosages of from about 10 mg BID to about 1000 mg BID, preferably from about 50 mg BID to about 500 mg BID, more preferably at a dose of from about 100 mg BID to about 300 mg BID.

Compounds as described in U.S. Pat. No. 5,384,330, including retigabine, can be administered orally using conventional pharmaceutical excipients or carriers, preferably coated or contained in hard or soft gelatin capsules. Examples of oral formulations contained in hard gelatin capsules can include those in which the active compound comprises from about 45% to 50%, by weight, of the formulation. Microcrystalline cellulose comprises from about 43% to about 47%, povidone comprises from about 3% to about 4%, and silicon dioxide and magnesium stearate each comprise from about 0.3% to about 0.7%, each by weight. Specific examples of capsules containing 50 mg, 100 mg and 200 mg may be formulated utilizing the following lists of components.

| Ingredient | Amount/Capsule |
|---|---|
| 50 mg Retigabine Capsules | |
| Retigabine | 50.0 mg |
| Microcrystalline Cellulose, NF | 45.5 mg |
| Povidone, USP | 3.5 mg |
| Silicon Dioxide, Colloidal, anhydrous, NF | 0.5 mg |
| Magnesium Stearate, EP | 0.5 mg |
| Theoretical Fill Weight | 100 mg |
| 100 mg Retigabine Capsules | |
| Retigabine | 100.0 mg |
| Microcrystalline Cellulose, NF | 91.0 mg |
| Povidone, USP | 7.0 mg |
| Silicon Dioxide, Colloidal, anhydrous, NF | 1.0 mg |
| Magnesium Stearate, EP | 1.0 mg |
| Theoretical Fill Weight | 200 mg |
| 200 mg Retigabine Capsules | |
| Retigabine | 200.0 mg |
| Microcrystalline Cellulose, NF | 182.0 mg |
| Povidone, USP | 14.0 mg |
| Silicon Dioxide, Colloidal, anhydrous, NF | 2.0 mg |
| Magnesium Stearate, EP | 2.0 mg |
| Theoretical Fill Weight | 400 mg |

The ingredients in the formulations above can be prepared using the following steps.

1) Weigh separately the active ingredient (retigabine), preferably screened through an 800 micron screen, and the microcrystalline cellulose components.

2) Prepare a granulation solution by dissolving the Povidone, USP in purified water.

3) Place the ingredients from Step 1 into a suitable blender and mix thoroughly.

4) Screen the mixture from Step 3 through a 1000 μm screen and place the screened mixture into the vessel of a fluidized bed granulator.

5) Heat the ingredients in the fluid bed granulator up to 27° C. product temperature while mixing.

6) Add the granulation solution from Step 2 to the fluid bed.

7) Dry the granulate in the fluid bed.

8) Weigh the colloidal silicon dioxide component, preferably screened through a 1000 μm screen, and the magnesium stearate component, preferably screened through a 600 μm screen.

9) Add the silicon dioxide and magnesium stearate components to the fluid bed granulator's vessel containing the dried granulate from Step 7 and mix the components thoroughly.

10) Screen the mixed components from Step 9, preferably through a 800 μm screen.

11) Transfer the final screened components into a suitable blender and mix thoroughly.

The final component mixture from Step 11 can then be coated, encapsulated or compressed into tablets utilizing conventional tablet excipients or carriers, as desired. It will be understood that oral dosage forms within the scope of this invention can be prepared using the components listed above in respective amounts according the dose of active ingredient in the particular formulation. For veterinary uses, the final mixture of Step 11 can be administered neat or mixed into foods acceptable to the animal in question. Further, the mixtures can be formulated into tablets, capsules or coated products, as described above, or integrated into conventional veterinary medicaments or food products.

For intravenous administration, the compounds from U.S. Pat. No. 5,384,330 described herein may be prepared and maintained in conventional lyophylized formulations and reconstituted prior to administration with an intravenously acceptable saline solution, such as a 0.9% saline solution. The pH of the intravenous formulation can be adjusted, as needed, with an intravenous and pharmaceutically acceptable acid, such as methanesulfonic acid.

The following demonstrates the ability of retigabine to open KCNQ potassium channels in mammalian tissue.

KNCQ1, 3 and 5 Expression and M-current Activity in Rat Urinary Bladder

Using quantitative rtPCR, the expression of KCNQ1, KCNQ3 and KCNQ5 potassium channels was identified in the rat urinary bladder. The highest levels of expression were seen in KCNQ5 (0.2±0.1 ng KCNQ5 mRNA/GAPDH mRNA). To further probe M-current activity in the bladder, retigabine (10 μM, M-current agonist) was tested in isolated bladder smooth muscle cells using standard patch-clamp techniques. Exposure to retigabine significantly increased an outward current that was insensitive to iberiotoxin and was associated with a membrane hyperpolarization of 17.8±3.0 mV (n=5). This hyperpolarization was reversed by the addition of linopirdine (50 μM an M-current antagonist) to the tissue bath. Retigabine relaxed isolated carbachol contracted rat bladder strips with an $IC_{50}$ of 3.5±0.9 μM (n=14). This relaxation was reversed by the M-current blockers linopirdine and XE-991.

KCNQ Potassium Channel Activity in Guinea Pig Ileum

Following the procedures of the previous example, the effects of retigabine on isolated precontracted guinea pig ileum preparations were studied. Sections of ileum were isolated from male guinea pigs and suspended in a tissue bath. One end of the tissue was anchored to the bottom of the bath, and the other end to a force transducer. Tissues were contracted with either 20 mM KCl or 200 nM carbachol. The KCNQ channel agonist retigabine was added to the tissue baths in increasing concentrations. Retigabine produced a concentration-dependent inhibition of contraction as follows:

| KCl Contracted | $IC_{50}$ = 7.1 ± 2 |
| Carbarchol Contracted | $IC_{50}$ = 5.4 ± 2 |

Both responses to retigabine were antagonized by the KNCQ channel blocker XE-991.

What is claimed is:

1. A method of treatment or inhibition of hyperactive gastrointestinal motility in a mammal, the method comprising administering to a mammal in need thereof a pharmacologically effective amount of a compound of the formula:

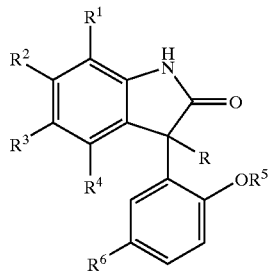

wherein:
R is hydrogen, hydroxy or fluoro;
$R^1$, $R^2$, $R^3$ and $R^4$ each are independently hydrogen, $C_{1-4}$ alkyl, halogen, trifluoromethyl, phenyl, p-methylphenyl or p-trifluoromethylphenyl; or $R^1$ and $R^2$, $R^2$ and $R^3$ or $R^3$ and $R^4$ are joined together to form a benzo-fused ring;

$R^5$ is hydrogen or $C_{1-4}$ alkyl; and
$R^6$ is chlorine or trifluoromethyl;
or a nontoxic pharmaceutically acceptable salt, solvate or hydrate thereof.

2. The method of claim 1 wherein the compound is selected from at least one of:

(±)-3-(5-Chloro-2-methoxyphenyl)-1,3-dihydro-3-hydroxy-6-(trifluoromethyl)-2H-indol-2-one;

(±)-3-(5-Chloro-2-methoxyphenyl)-1,3-dihydro-6-(trifluoromethyl)-2H-indol-2-one;

(±)-3-(5-Chloro-2-hydroxyphenyl)-1,3-dihydro-3-hydroxy-6-(trifluoromethyl)-2H-indol-2-one;

(±)-3-(5-Chloro-2-hydroxyphenyl)-1,3-dihydro-6-(trifluoromethyl)-2H-indol-2-one;

(±)-3-(5-Chloro-2-hydroxyphenyl)-4,6-dichloro-1,3-dihydro-3-hydroxy-2-H-indol-2-one;

(±)-3-(5-Chloro-2-hydroxyphenyl)-1,3-dihydro-3-hydroxy-7-(trifluoromethyl)-2H-indol-2-one;

(±)-3-(5-Chloro-2-hydroxyphenyl)-1,3-dihydro-3-hydroxy-4-trifluoromethyl)2H-indol-2-one;

(±)-1,3-Dihydro-3-hydroxy-3-[2-hydroxy-5-(trifluoromethyl)phenyl]-6-(trifluoromethyl)-2H-indol-2-one;

(±)-3-(5-Chloro-2-hydroxyphenyl)-1,3-dihydro-3-hydroxy-4,6-bis(trifluoromethyl)-2H-indol-2-one;

(−)-3-(5-Chloro-2-methoxyphenyl)-1,3-dihydro-3-hydroxy-6-(trifluoromethyl)-2H-indol-2-one;

(±)-3-(5-Chloro-2-hydroxyphenyl)-1,3-dihydro-3-hydroxy-6-(trifluoromethyl)2H-indol-2-one;

(−)-3-(5-Chloro-2-hydroxyphenyl)-1,3-dihydro-3-hydroxy-6-(trifluoromethyl)2H-indol-2-one;

(±)-3-(5-Chloro-2-methoxyphenyl)-1,3-dihydro-3-fluoro-6-(trifluoromethyl)2H-indol-2-one;

(±)-3-(5-Chloro-2-hydroxyphenyl)-1,3-dihydro-3-hydroxy-2H-benz[g]indol-2one;

(±)-3-(5-Chloro-2-hydroxyphenyl)-1,3-dihydro-6-phenyl-2H-indol-2-one;

(±)-3-(5-Chloro-2-hydroxyphenyl)-1,3-dihydro-2H-benz[g]indol-2-one;

(±)-3-(5-Chloro-2-methoxyphenyl)-1,3-dihydro-3-fluoro-6-phenyl-2H-indol-2-one;

(±)-3-(5-Chloro-2-methoxyphenyl)-1,3-dihydro-3-fluoro-6-iodo-2H-indol-2one;

(±)-3-(5-Chloro-2-hydroxyphenyl)-1,3-dihydro-6-(4-methylphenyl)-2H-indol-2-one;

(±)-3-(5-Chloro-2-methoxyphenyl)-1,3-dihydro-3-fluoro-7-(trifluoromethyl)-2H-indol-2-one;

(±)-3-(5-Chloro-2-hydroxyphenyl)-1,3-dihydro-2H-benz[e]indol-2-one;

(±)-3-(5-Chloro-2-methoxyphenyl)-1,3-dihydro-3-fluoro-5-methyl-2H-indol-2-one;

(±)-3-(5-Chloro-2-methoxyphenyl)-1,3-dihydro-3-fluoro-4,6-bis(trifluoromethyl)-2H-indol-2-one;

(±)-5-Bromo-3-(5-chloro-2-methoxyphenyl)-1,3-dihydro-3-fluoro-2H-indol-2one;

(±)-3-(5-Chloro-2-hydroxyphenyl)-1,3-dihydro-6-[4-(trifluoromethyl)phenyl]-2H-indol-2-one;

(±)-3-(5-Chloro-2-hydroxyphenyl)-1,3-dihydro-2H-indol-2-one;

(±)-5-Bromo-3-(5-chloro-2-methoxyphenyl)-1,3-dihydro-3-hydroxy-2H-indol-2-one;

(±)-3-(5-Chloro-2-hydroxyphenyl)-4,6-dichloro-1,3-dihydro-2H-indol-2-one;

(±)-3-(5-Chloro-2-methoxyphenyl)-1,3-dihydro-3-hydroxy-6-iodo-2H-indol-2-one;

(±)-3-(5-Chloro-hydroxyphenyl)-1,3-dihydro-6-iodo-2H-indol-2-one;

(±)-3-(5-Chloro-2-methoxyphenyl)-1,3-dihydro-3-hydroxy-2H-benz[f]indol-2one;

(±)-3-(5-Chloro-2-hydroxyphenyl)-1,3-dihydro-3-hydroxy-2H-benz[f]indol-2one; or (±)-3-(5-Chloro-2-hydroxyphenyl)-1,3-dihydro-2H-benz[f]indol-2-one;

or a pharmaceutically acceptable salt form thereof.

3. The method of claim 1 wherein the mammal is a human.

4. The method of claim 1 wherein the mammal is feline or canine.

5. The method of claim 1 wherein the hyperactive gastrointestinal motility in a mammal is associated with irritable bowel syndrome.

6. The method of claim 1 wherein the hyperactive gastrointestinal motility in a mammal is associated with Crohn's disease.

7. The method of claim 1 wherein the hyperactive gastrointestinal motility in a mammal is associated with diarrhea.

8. The method of claim 1 wherein the hyperactive gastrointestinal motility in a mammal is associated with colitis.

9. The method of claim 1 wherein the hyperactive gastrointestinal motility in a mammal is associated with postprandial urgency or postprandial accentuation of diarrhea.

* * * * *